(12) United States Patent
Elliott

(10) Patent No.: US 7,044,962 B2
(45) Date of Patent: May 16, 2006

(54) IMPLANTABLE PROSTHESIS WITH DISPLACEABLE SKIRT

(75) Inventor: Chris Elliott, Hopkinton, MA (US)

(73) Assignee: SCIMED Life Systems, Inc., Maple Grove, MN (US)

( * ) Notice: Subject to any disclaimer, the term of this patent is extended or adjusted under 35 U.S.C. 154(b) by 244 days.

(21) Appl. No.: 10/179,535

(22) Filed: Jun. 25, 2002

(65) Prior Publication Data

US 2003/0236567 A1 Dec. 25, 2003

(51) Int. Cl.
*A61F 2/06* (2006.01)

(52) U.S. Cl. ..................................... 623/1.13
(58) Field of Classification Search .............. 623/1.15, 623/1.35, 1.12, 1.13; 606/153–156
See application file for complete search history.

(56) References Cited

U.S. PATENT DOCUMENTS

| | | | |
|---|---|---|---|
| 3,818,511 | A | 6/1974 | Goldberg et al. |
| 4,662,890 | A | 5/1987 | Burton |
| 5,425,739 | A | 6/1995 | Jessen |
| 5,476,506 | A | 12/1995 | Lunn |
| 5,522,881 | A | 6/1996 | Lentz |
| 5,562,727 | A | 10/1996 | Turk et al. |
| 5,591,195 | A | 1/1997 | Taheri et al. |
| 5,628,784 | A | 5/1997 | Strecker |
| 5,769,882 | A | 6/1998 | Fogarty et al. |
| 5,843,158 | A | 12/1998 | Lenker et al. |
| 5,944,750 | A | 8/1999 | Tanner et al. |
| 6,015,431 | A | 1/2000 | Thornton et al. |
| 6,056,762 | A | 5/2000 | Nash et al. |
| 6,096,071 | A | 8/2000 | Yadav |
| 6,258,120 | B1 | 7/2001 | McKenzie et al. |
| 6,306,163 | B1 | 10/2001 | Fitz |
| 6,331,188 | B1 | 12/2001 | Lau et al. |
| 2001/0037142 | A1 | 11/2001 | Stelter et al. |

FOREIGN PATENT DOCUMENTS

| | | |
|---|---|---|
| WO | WO 96/39104 | 12/1996 |
| WO | WO 98/27895 | 7/1998 |
| WO | WO 99/51165 | 10/1999 |
| WO | WO 01/26582 | 4/2001 |

OTHER PUBLICATIONS

"Endovascular Stent-Graft in Abdominal Aortic Aneurysms: The Relationship between Patent Vessels that Arise from the Aneurysmal Sac and Early Endoleak" by Fan et al., Radiology 2001, vol. 218, No. 1, pp. 176-182.
Copy of International Search Report from International Application No. PTC/US03/13472 dated Sep. 5, 2003.

*Primary Examiner*—(Jackie) Tan-Uyen T. Ho
(74) *Attorney, Agent, or Firm*—Hoffmann & Baron, LLP

(57) ABSTRACT

An implantable prosthesis is provided having a radially-expandable tubular body and at least one skirt extending therefrom. The skirt terminates in a peripheral edge, wherein at least portions of the peripheral edge are free and displaceable to a greater diameter of the tubular body. Thus, with the implantable prosthesis being a stent-graft used to treat an aortic aneurysm (e.g., abdominal aortic aneurysm ("AAA")), the skirt may be used to inhibit Type I endoleaks upon its selective displacement in response to irregular aortic shaping and/or aneurysm neck expansion. The skirt may actively inhibit Type I endoleaks by forming a physical barrier against flow between the tubular body and the aortic wall. In addition, the skirt may passively inhibit endoleak formation by sufficiently restricting blood flow to allow coagulation and clot formation, which would act as a barrier against endoleakage.

19 Claims, 7 Drawing Sheets

IMPLANTABLE PROSTHESIS WITH DISPLACEABLE SKIRT

FIELD OF THE INVENTION

This invention relates to tubular prostheses, including, but not limited to, endovascular grafts and stent-grafts, for maintaining patency of blood vessels and treating aneurysms (e.g., aortic aneurysms), and tubular conduits for maintaining patency in other bodily passageways.

BACKGROUND OF RELATED TECHNOLOGY

It is known in the prior art to use endovascular prostheses to treat aortic aneurysms (e.g., abdominal aortic aneurysms ("AAA")). Such treatment includes implanting a stent, or stent-graft, within the diseased vessel to by-pass the anomaly. An aneurysm is a sac formed by the dilation of the wall of the artery, which may be congenital, but usually is caused by disease and, occasionally, by trauma. With reference to FIG. 1, sac 1 of aneurysm A is defined by dilated portions 2 of aorta AA. With the collection of blood and other embolic material in the sac 1, and being subjected to hemodynamic pressure, the aneurysm A may rupture, if untreated, causing internal bleeding.

Techniques had been developed in the prior art where diseased portions of a blood vessel, such as with an aneurysm, were ablated and replaced with a prosthetic member, such as that shown in U.S. Pat. No. 4,938,740 to Melbin. This technique, however, required open surgery. As an improvement over this technique, endovascular emplacement techniques have been developed to implant grafts and stent-grafts into a vessel from a remote puncture site, thereby obviating the need for open surgery. For example, as shown in FIG. 1, an endovascular prosthesis 3 (stent or stent-graft) is positioned to by-pass the aneurysm A with ends 4, 5 of the prosthesis being in contiguous contact with healthy portions of the aorta AA, the prosthesis 3 having been introduced endovascularly (e.g., with a catheter). Accordingly, if the aneurysm A were to rupture, blood flow through the aorta AA would be uninterrupted, and internal bleeding generally avoided. Aortic aneurysms which commonly form between the renal arteries RA and the iliac arteries IA are referred to as abdominal aortic aneurysms ("AAA") (shown in FIG. 1). Other aneurysms are possible in the aorta, such as thoracic aortic aneurysms ("TAA") and aortic uni-iliac ("AUI") aneurysms.

Although considerable success has been enjoyed with stent and stent-graft performance, failures in the form of endoleaks have been noted and predominantly classified in four classes: Types I–IV. Type I failures relate to leaks between the vascular prosthesis and the vessel wall. For example, with reference to FIG. 1, a Type I failure would be blood weeping about the end 4 of the prosthesis 3 into the sac 1. Type I failures have been found to be caused by a continual expansion of the aneurysm neck (portion of the aorta AA extending cephalad or caudad from the aneurysm A). This expansion rate has been estimated to be about 1 mm/year. With the aneurysm neck expanding beyond the natural resting diameter of the prosthesis 3, passageway(s) are defined about the prosthesis 3 in communication with the aneurysm sac 1. Additionally, Type I endoleaks are also caused when circular prostheses are implanted in non-circular aortic lumens, which may be caused by irregular vessel formation and/or calcified topography of the lumen of the aorta AA.

A Type II failure involves blood flowing into the aneurysm sac through collateral vessels. Again, with reference to FIG. 1, the sac 1 may be in fluid communication with blood vessels BV, other than the aorta AA. Typically, lumbar arteries are in fluid communication (directly or indirectly) with an aneurysm sac. Since blood flow out of the sac 1 is prevented, hemodynamic pressure away from the sac 1 is not present. However, because of hemodynamic pressure within blood vessels in communication with the sac 1, blood flow, nevertheless, is directed into the sac 1 (as shown by arrows). A technique has been developed in the prior art which calls for embolizing the blood vessels BV, such as with embolus coils, thereby isolating the sac 1 from collateral blood flow. However, an additional procedure would be required for embolization.

A Type III failure is a mechanical failure, wherein a hole may be ripped into the prosthesis (e.g., excessive wear at a metal/non-metal (fabric or polymer) interface) or poor integrity exists at a connection, or connections, between modular components of a prosthesis, (e.g., extensions may be connected to the prosthesis to obtain improved securement in one or both of the iliac arteries IA.) For example, as shown in FIG. 1, a hole 6 may be torn into the prosthesis 2, or poor sealing is obtained at the connection between the prosthesis 3 and an extension 7.

A Type IV failure relates to excessive prosthesis porosity, wherein blood seeps through the prosthesis regardless of the integrity of sealing and mechanical connections.

As can be readily appreciated, even with the successful implantation of an endovascular prosthesis, failures may occur thereafter. It has been found that Type I failures may affect up to 5–10% of all implanted prostheses. Accordingly, there is a clear need for an endovascular prosthesis which can reduce the likelihood of, and ideally eliminate, Type I failures.

SUMMARY OF THE INVENTION

To overcome shortcomings in the prior art, and to limit Type I endoleaks, an implantable prosthesis is provided having a radially-expandable tubular body and at least one skirt extending therefrom. The skirt terminates in a peripheral edge, wherein at least portions of the peripheral edge are free and displaceable to a greater diameter than the tubular body. Thus, with the implantable prosthesis being a stent-graft used to treat an aortic aneurysm (e.g., abdominal aortic aneurysm ("AAA")), the skirt may be used to inhibit Type I endoleaks upon its selective displacement in response to irregular aortic shaping and/or aneurysm neck expansion. The skirt may actively inhibit Type I endoleaks by forming a physical barrier against flow between the tubular body and the aortic wall. In addition, the skirt may passively inhibit endoleak formation by sufficiently restricting blood flow to allow coagulation and clot formation, which would act as a barrier against endoleakage. Endothelial cell ingrowth into the skirt may also occur providing a cellular barrier against endoleakage.

The skirt may be supported by a scaffold, such as a plexus of elements arranged in any known pattern used in stent manufacturing. Alternatively, the skirt may have limited support, such as by a plurality of circumferentially-spaced tines. As a further alternative, the skirt need not be supported. Furthermore, the skirt may be formed to be displaceable into various shapes, including being tapered or cylindrical; or, may be formed with portions of different geometric configurations, such as a first portion which extends circumferentially outwardly from the prosthesis, with a second portion that it is coextensive with the prosthesis. The circumferential portion may be trough-shaped such that force applied thereto by blood flow may be re-directed to define a radial force directed away from the prosthesis. Such an outward radial force may be used to press portions of the peripheral edge against the blood vessel wall in reinforcing a seal therewith.

These and other features will be better understood through a study of the following detailed description and accompanying drawings.

DETAILED DESCRIPTION OF THE INVENTION

The invention herein provides an implantable prosthesis which may be used as a graft to replace a portion of a bodily passageway (e.g., vascular graft), or may be used within a bodily passageway to maintain patency thereof, such as an endovascular stent-graft. In addition, the prosthesis can be used in other bodily applications, such as the esophagus, trachea, colon, biliary tract, urinary tract, prostate and the brain.

Figure 1:
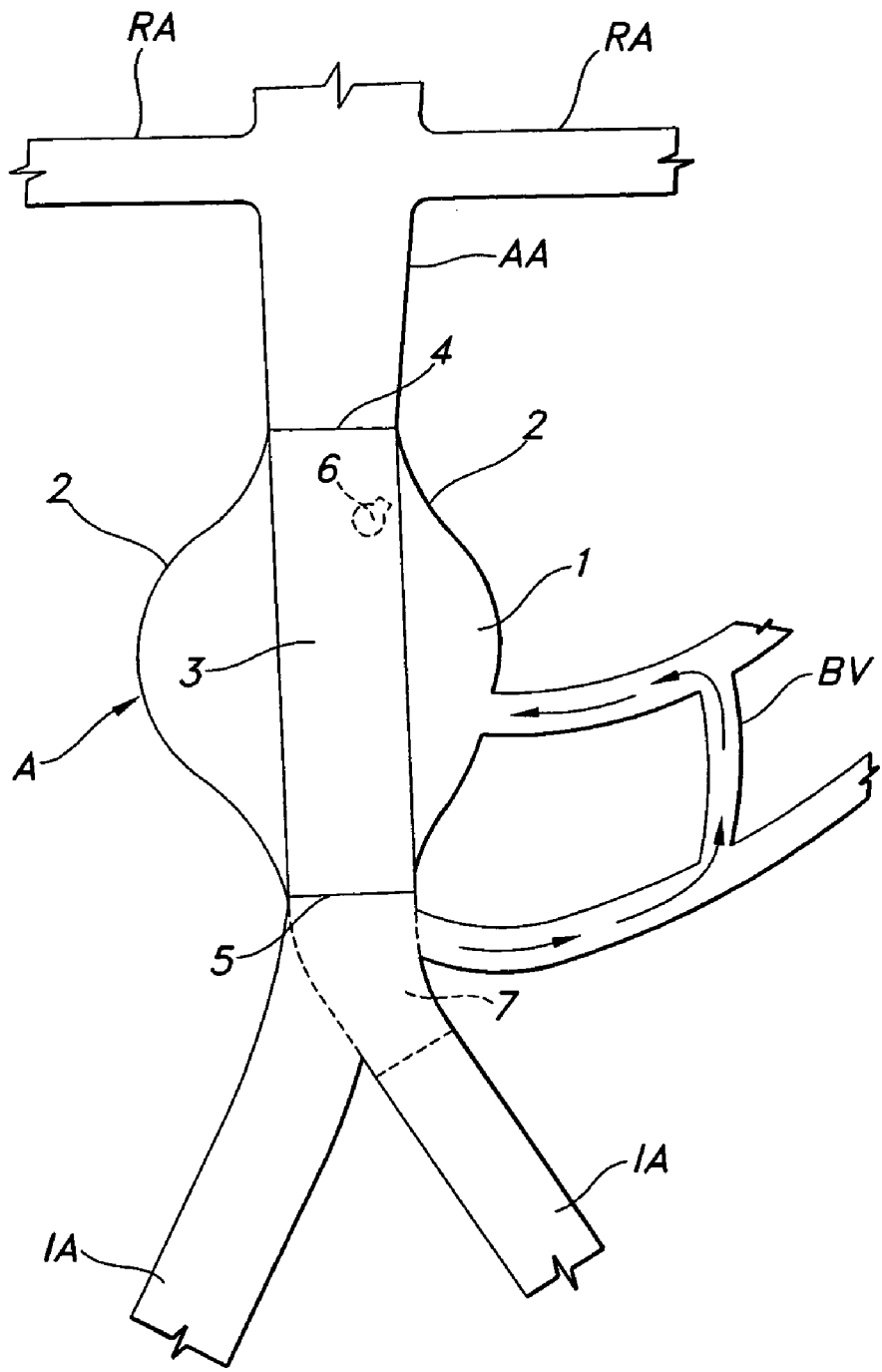
FIG. 1 is a schematic of an aortic aneurysm with a stent-graft implanted therein.
Figure 2A:
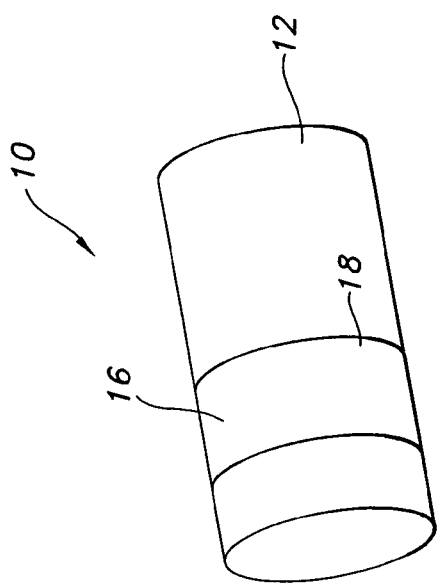
FIGS. 2a and 2b show implantable prostheses.
Figure 2B:
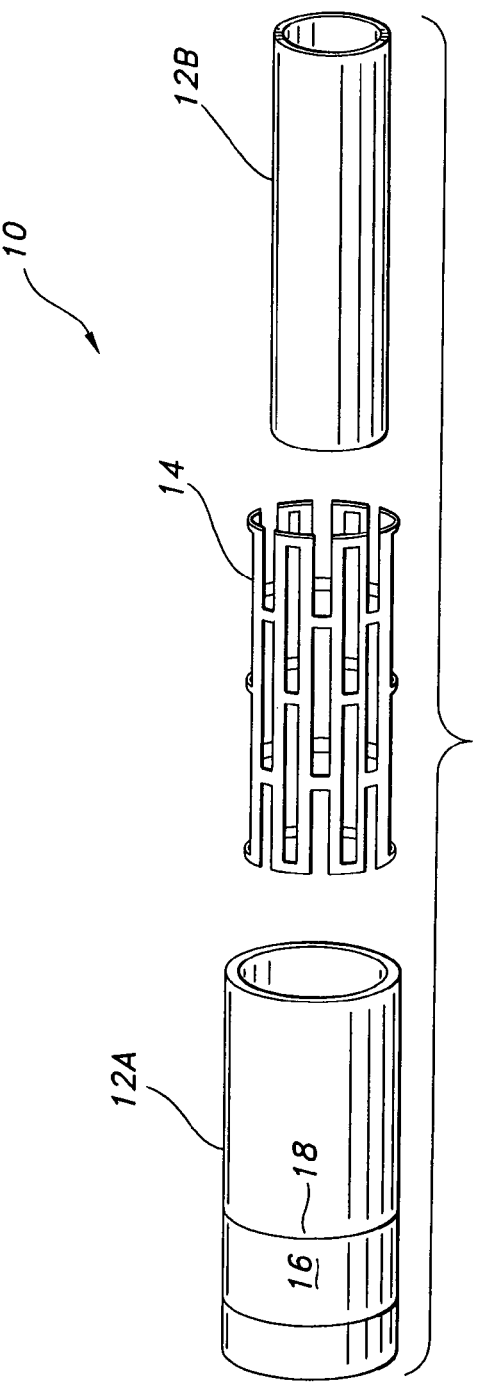

The implantable prosthesis of the subject invention is representatively depicted in FIGS. 2a–2b and generally designated with the reference numeral 10. The prosthesis 10 is particularly well suited to act as an endovascular graft or stent-graft. The prosthesis 10 includes a tubular body 12 which is preferably radially-expandable. The tubular body 12 may be composed of one or more layers of known materials used in endovascular graft formation, including, but not limited to a polymeric material (e.g., polytetrafluoroethylene), a textile material (e.g., polyethylene terephthalate (PET)), natural tissue (e.g., saphenous vein or collagen), and combinations thereof. As with known endovascular graft and stent-graft construction, the tubular body 12 is preferably collapsible and radially-expandable to a natural resting diameter. In addition, as shown in FIG. 2b, the prosthesis 10 may also include a radially expandable support member 14, and one or more tubular bodies 12A, 12B. The radially expandable support member 14 may be disposed interiorly of the tubular body 12A; exteriorly of the tubular body 12B; or interposed between one or more of the tubular bodies 12A, 12B. Optionally, multiple radially expandable support members 14 may be provided at one or more of the aforementioned locations. The radially expandable support member 14 may be fixed to the tubular bodies 12A, 12B using any technique known to those skilled in the art, such as bonding (e.g., with a thermoplastic fluoropolymer adhesive (such as FEP)). Additionally, with the radially expandable support member 14 being interposed between the tubular bodies 12A, 12B, the tubular bodies 12A, 12B may be fixed together through any interstices formed in the radially expandable support member 14. The radially expandable support member(s) 14 will impart the prosthesis 10 (and thus any of the tubular bodies 12; 12A, 12B) with a natural resting diameter. In further describing the invention, reference will be made to a tubular body 12 in the singular; it is to be understood that the reference to a singular tubular body 12 includes reference to the variations of the prosthesis described, including use of multiple tubular bodies 12A, 12B and one or more of the radially expandable support member 14.

The radially expandable support member 14 may be of any construction known in the prior art which can maintain patency of the prosthesis 10. For example, as shown in FIG. 2b, the radially expandable support member 14 may be a stent. The particular stent 14 shown in FIG. 2b is fully described in commonly assigned U.S. Pat. No. 5,693,085 to Buirge et al., and the disclosure of U.S. Pat. No. 5,693,085 is incorporated by reference herein. The stent may be an intraluminally implantable stent formed of: a metal, such as stainless steel, tantalum, or niobium; a temperature-sensitive material, such as Nitinol; or, alternatively, a super elastic alloy or suitable polymer. Although a particular stent construction is shown with reference to the present invention, various stent types and stent constructions may be employed for the uses anticipated herein. Among the various useful radially expandable members 14 included are, without limitation, self-expanding stents and balloon expandable stents. The stents may be capable of radially contracting as well. Self-expanding stents include those that have a spring-like action which causes the stent to radially expand or stents which expand due to the memory properties of the stent material for a particular configuration at a certain temperature. Other materials are of course contemplated such as platinum, gold, titanium, and other biocompatible materials, as well as polymeric stents. The configuration of the radially expandable support member 14 may also be chosen from a host of geometries. For example, wire stents can be fastened in a continuous helical pattern, with or without wave-like forms or zig-zags in the wire, to form a radially deformable stent. Also, individual rings or circular members can be linked together such as by struts, sutures, or interlacing or locking of the rings to form a tubular stent.

Furthermore, the prosthesis 10 may be used with additional layers which may be formed of polymeric material, textile and/or natural tissue, such as natural vein or collagen. Furthermore, any layer or portion of the prosthesis 10 may be impregnated with one or more therapeutic and pharmacological substances prior to implantation of the prosthesis 10 for controlled release over an extended duration. It is anticipated that the prosthesis 10 can be partially or wholly coated with hydrophilic or drug delivery-type coatings which facilitate long-term healing of diseased vessels. Such a coating is preferably bioabsorbable, and is preferably a therapeutic agent or drug, including, but not limited to: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor promotors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

With reference to FIGS. 2a and 2b, the prosthesis 10 is provided with at least one skirt 16 (which may be formed in various geometric configurations) that extends from the tubular body 12. The skirt 16 terminates in a peripheral edge 18 that is spaced from a juncture between the skirt 16 and the tubular body 12. As described more fully below, the peripheral edge 18 is free and displaceable to a greater diameter than the diameter of the tubular body 12, particularly at its natural resting diameter. In this manner, portion(s) of the peripheral edge 18 can be displaced to contact, and form a seal with a surrounding wall. Irregularities and/or wall displacement (occurring such as from aneurysm neck expansion) can be responded to by the skirt 16 in minimizing endoleaks about the prosthesis 10.

The skirt 16 may be formed of any material used in preparing the tubular body 12. In addition, the skirt 16 may be coated with, for example, collagen, fibrin, hyaluronic acid, chitosan, and/or other polysaccharide. The skirt 16 may act as a passive barrier against endoleaks by encouraging coagulation and clot formation by being coated with fibrin. Accordingly, the skirt 16 need not form a completely tight mechanical (i.e., "active") seal with the surrounding wall, but rely on a passive clot barrier to inhibit endoleakage. The skirt 16 may also be formed to encourage cell ingrowth, such as endothelial cell ingrowth, with surface configurations (e.g., roughened surface) and/or by being formed or coated with material susceptible to cell ingrowth (e.g., velour). With cellular ingrowth, the skirt 16 may attach to a surrounding wall, and not only support a cellular barrier against endoleakage, but also responsively move with the surrounding wall due to its connection therewith.

One or more of the skirts 16 may be provided to form seals along various points about the prosthesis 10. In addition, the skirt 16 may be positioned to seal an appropriate point or points relative to the prosthesis 10. The skirt 16 may also be oriented as needed, for example, relative to blood flow. The prosthesis 10 may be used in other blood vessels, and, as indicated above, in other bodily passageways. As will be appreciated by those skilled in the art, the prosthesis 10 can be used to form seals not only at points cephalad of an abdominal aortic aneurysm, but also points caudad (e.g., at the iliac arteries).

As will also be appreciated by those skilled in the art, the skirt 16 may be formed in various configurations to allow for a free peripheral edge 18 which is at least partially displaceable to a larger diameter than the tubular body 12. Various embodiments of the skirt 16 are described herein to illustrate operation of the invention, although other embodiments may be resorted to consistent with the teachings herein.

Figure 3A:
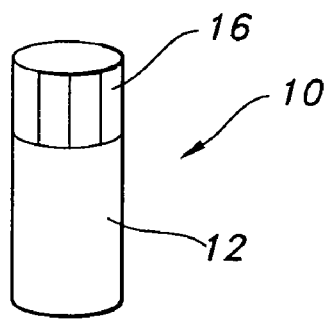
FIGS. 3a–3e show a first embodiment of the subject invention.
Figure 3B:
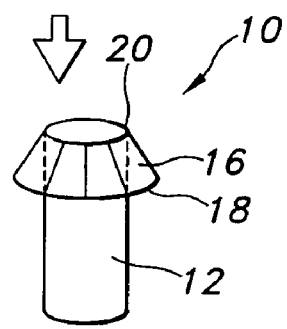
Figure 3C:
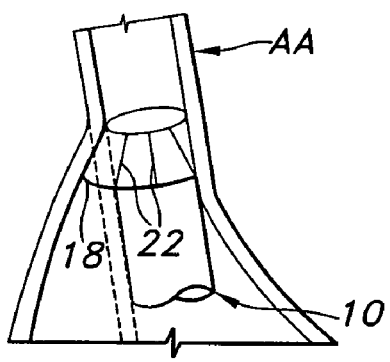
Figure 3D:
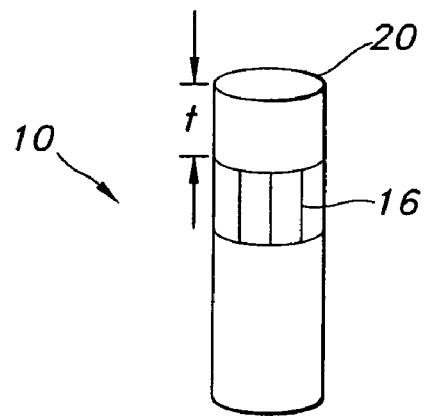

With reference to FIGS. 3a–3e, a first embodiment of the skirt 16 is shown, which is tapered downwardly relative to the tubular body 12. Thus, with reference to FIG. 3b, the skirt 16 is intended to be tapered to a greater diameter in a direction of blood flow, as represented by the arrow. The skirt 16 is joined to the tubular body 12 at a juncture located at, or in proximity to, an upstream end of the tubular body relative to blood flow. FIGS. 3a–3c show the skirt being joined at an upstream end 20, while FIG. 3d shows the skirt 16 being spaced from the end 20. It is preferred that the skirt 16 be spaced a distance t in the range of 2–15 mm from the end 20.

In an initial state, as shown in FIG. 3a, the skirt 16 lies flat or relatively flat in overlapping a portion of the tubular body 12. With this configuration, the profile of the prosthesis 10 can be minimized in easing implantation thereof. Once implanted, such as in an aorta AA, as shown in FIG. 3c, at least a portion of the peripheral edge 18 may be displaced in response to an irregularity in the aorta AA lumen and/or aneurysm neck expansion (FIG. 3c shows a portion of the aorta AA having been displaced from the original position shown in dashed lines due to aneurysm neck expansion). The tubular body 12 will expand maximally to its natural resting diameter in response to the lumenal irregularities and/or expansion. The skirt 16 allows for expansion beyond that natural resting diameter.

Figure 3E:
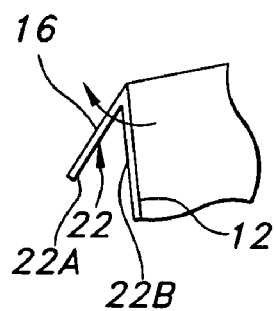

With the first embodiment, the peripheral edge 18 is displaced by scaffold 22 which supports the skirt 16. It is preferred that limited support be provided for the skirt 16; as such, the scaffold 22 preferably includes a plurality of circumferentially-spaced tines which are self-expanding, either due to inherent spring action and/or due to memory properties of the constituent material. The skirt 16 is joined to the tubular body 12 using any technique known to those skilled in the art, such as bonding. To facilitate radial expansion of the scaffold 22, individual members thereof must be mounted to the tubular body 12 such as to provide sufficient counterforce to allow for radial expansion. It is preferred that point contacts between the members of the scaffold 22 and the tubular body 12 be avoided. With reference to FIG. 3e, the scaffold 22 may include scaffold members 22A supporting the skirt 16, and counterforce members 22B attached to the tubular body 12. Expansion of the skirt 16 is attained by displacing the scaffold members 22A, with the counterforce members 22B providing counterforce to allow such displacement. The tines of the scaffold 22 are shown to be straight in the figures, but may be of other shapes, such as wavy, S-shaped, bent and so forth. As an alternative configuration, the skirt 16 may be more fully supported, wherein the scaffold 22 includes a plexus of elements (e.g., wire members) arranged in a typical stent configuration. The elements may be of any construction which provides sufficient stiffness to allow for displacement of the skirt 16. For example, the elements may be of polymeric material or textile (e.g., the skirt 16 may be pleated to define the scaffolding 22). Here, selected elements may be formed and appropriately attached to provide counterforce.

With radial expansion of the skirt 16, as shown in FIG. 3c, radial force is directed outwardly through the peripheral edge 18 to facilitate seal formation against a surrounding wall. In this manner, an active mechanical seal may be formed against endoleakage. Moreover, portion(s) of the skirt 16 may be responsively displaced where needed.

With reference to FIGS. 4a–4e, a second embodiment of the subject invention is shown, where the skirt 16 is formed with a generally cylindrical shape. More particularly, with reference to FIG. 4b, the skirt 16 is shown in an expanded state, wherein a first portion 24 of the skirt 16 extends radially outwardly from the tubular body 12, and a second portion 26 of the skirt 16 depends downwardly therefrom to terminate at the peripheral edge 18. The first portion 24 is supported by the scaffold 22, which as shown in the figures, is preferably a plurality of circumferentially-spaced arcuate tines. As shown in dashed lines in FIG. 4a, the tines alternatively may be formed straight, or in another shape. As a further alternative, and as with the first embodiment, the scaffold 22 may also be a plexus of various elements.

Preferably, the second portion 26 is unsupported, although the scaffold 22 may extend from the first portion 24 to at least partially support the second portion 26; or, alternatively, a separate scaffold (not shown) may be provided to support the second portion 26.

Figure 4A:
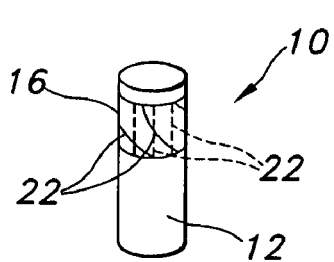
FIGS. 4a–4e show a second embodiment of the subject invention.
Figure 4B:
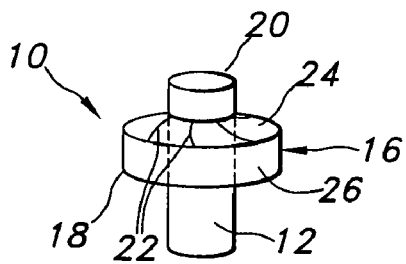
Figure 4C:
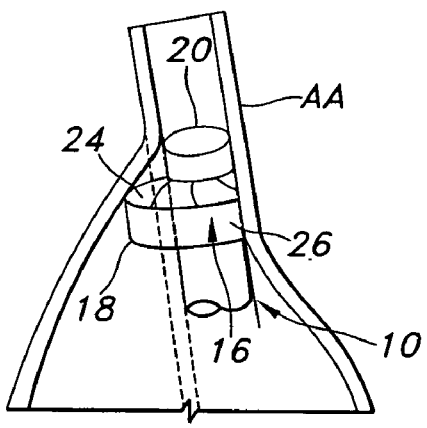

As with the first embodiment, the skirt 16 is preferably located to be spaced at a short distance (2–15 mm) from the proximal end 20, although it may also be located at the end 20. With reference to FIG. 4a, the prosthesis 10 is implanted with the skirt 16 being in a relatively flat state. Once implanted, as shown in FIG. 4c, the skirt 16 expands to prevent endoleakage in a similar manner as described above with respect to the first embodiment. With arcuate tines, however, skirt displacement will also include a rotational element.

Figure 4D:
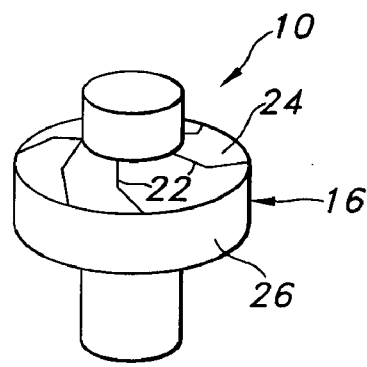
Figure 4E:
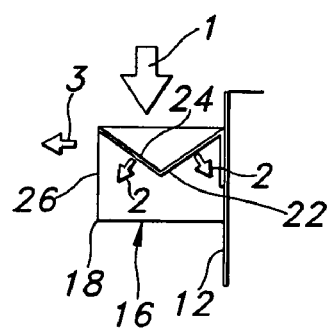

As a variation of the second embodiment, the first portion 24 may be trough-shaped as shown in FIGS. 4d and 4e. In an expanded, or partially expanded state, the scaffold 22 is configured such that the first portion 24 includes a trough-shaped depression which may be V-shaped, U-shaped or the like. As shown in FIG. 4e, with the skirt 16 being at least partially expanded, blood flow that bypasses the tubular body 12 (which would normally constitute endoleakage) applies hemodynamic pressure as indicated by arrow 1 into the first portion 24 which, then results in normal force applied against the sides of the trough (arrows 2). These forces cumulatively attempt to flatten the first portion 24, resulting in further radial expansion (arrow 3) of the skirt 16, and, thus, a tighter seal against a surrounding wall. With the alternative variation of FIGS. 4d and 4e, potential endoleakage is converted to increased sealing force.

With reference to FIGS. 5a–5e, a further embodiment of the subject invention is depicted, wherein the skirt 16 is formed to be tapered upwardly. Generally, the same comments apply as set forth with respect to the first embodiment depicted in FIGS. 3a–3d, except that the skirt 16 is inverted from that shown in the first embodiment. In addition, with respect to the third embodiment, it is preferred that the skirt 16 not be supported by a scaffold 22, although optionally it may be so supported. Furthermore, drain holes 28 may be formed through the tubular body at locations below the skirt 16 so as to allow blood flow trapped by the skirt 16 to be re-introduced into the main stream of blood flow through the tubular body 12.

Figure 5A:
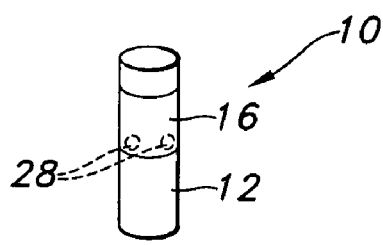
FIGS. 5a–5e show a third embodiment of the subject invention.
Figure 5B:
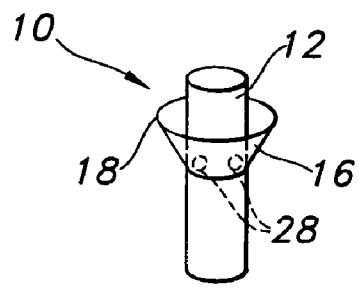
Figure 5C:
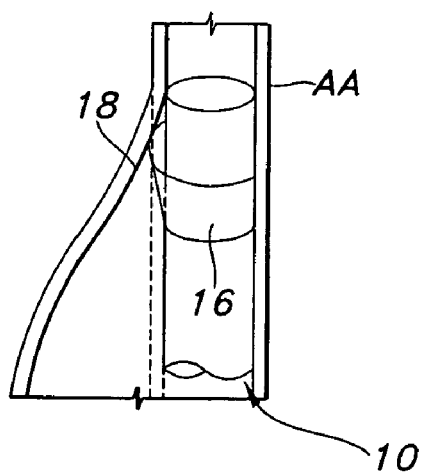
Figure 5D:
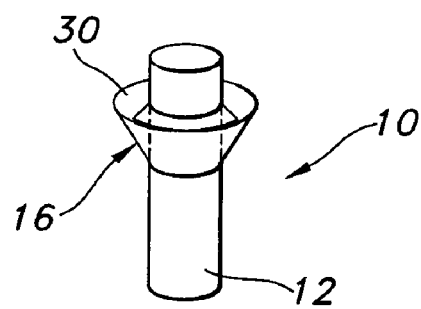

Without scaffold 22, expansion of the skirt 16 occurs under pressure of endoleakage. As shown in FIG. 5c, a portion or portions of the peripheral edge 18 are separated from the tubular body 12 in response to such stray blood flow.

Figure 5E:
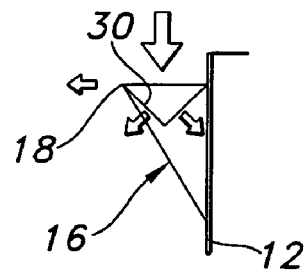

As a variation of the third embodiment, a trough-shaped first portion 30 may be provided, similarly configured to that disclosed with respect to the second embodiment. As shown in FIG. 5e, the first portion 30 is preferably unsupported by any scaffold, but is responsive to blood flow pressure to cause radially-outward expansion.

Figure 6:
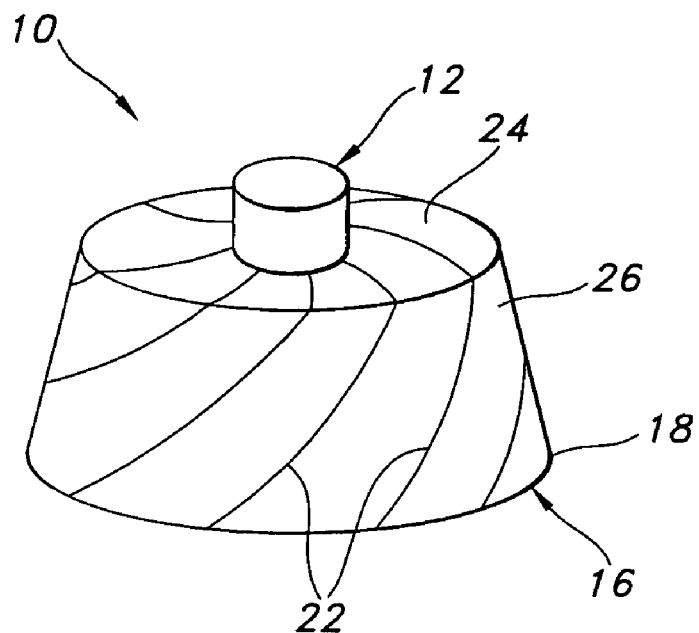
FIG. 6 shows a fourth embodiment of the subject invention.

With reference to FIG. 6, a fourth embodiment of the subject invention is shown which is similar to the variation of the second embodiment shown in FIGS. 4d and 4e. Particularly, the first portion 24 is trough-shaped and formed as discussed above. The second portion 26 is, however, tapered downwardly and preferably away from the tubular body 12. In contrast, the second portion 26, as shown in FIGS. 4d and 4e, is generally parallel to the tubular body 12. To enable the tapered shape of the second portion 26, scaffold 22 is provided to support it. As shown in FIG. 6, the scaffold 22 may extend continuously from the first portion 24. Alternatively, a separate scaffold (not shown) may be provided to support the second portion 26. Other geometric configurations and combinations of geometric configurations can be resorted to in forming the skirt 16.

Figure 7:
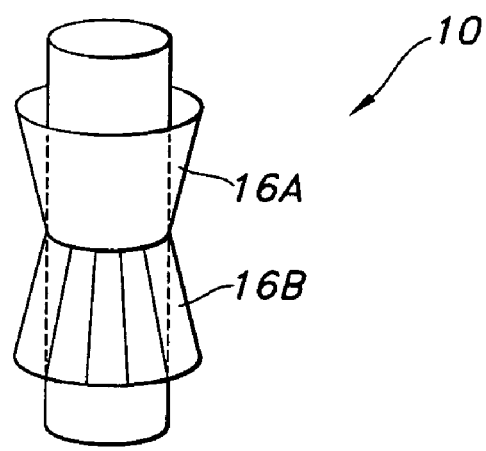
FIG. 7 shows a prosthesis including skirts formed in accordance with the first and third embodiments of the subject invention.
Figure 8:
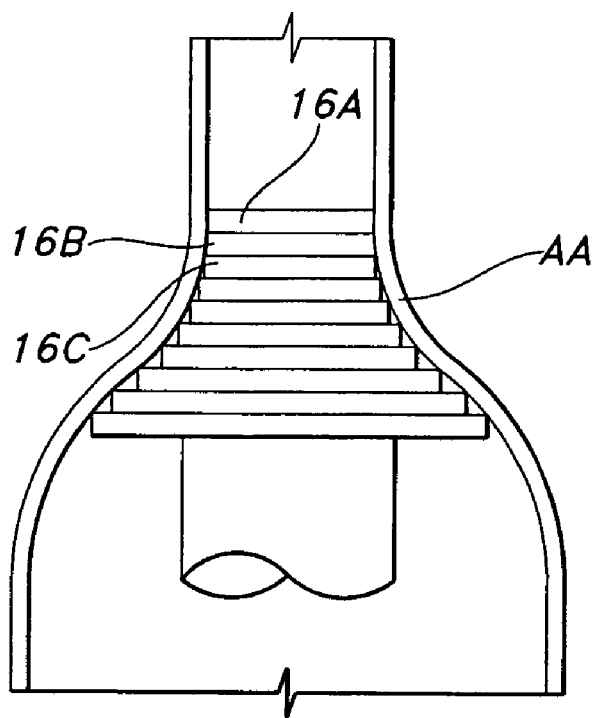
FIG. 8 shows a prosthesis including a plurality of skirts serially arranged formed in accordance with the second embodiment of the subject invention.

In addition, as will be understood by those skilled in the art, more than one of the skirts 16 may be provided on the tubular body 12 to provide redundant seals. For example, with reference to FIG. 7, the prosthesis is provided with one of the skirts 16a (formed in accordance with the third embodiment herein) and, a second of the skirts 16b (formed in accordance with the first embodiment herein). As such, the second skirt 16b provides a redundant seal to prevent endoleakage which may bypass the skirt 16a. Other combinations of skirts and skirt embodiments are possible. For example, with respect to FIG. 8, a plurality of the skirts 16A, 16B, 16C . . . formed in accordance with the second embodiment herein, may be serially arranged.

As is readily apparent, numerous modifications and changes may readily occur to those skilled in the art, and hence it is not desired to limit the invention to the exact construction operation as shown and described, and accordingly, all suitable modification equivalents may be resorted to falling within the scope of the invention as claimed.

What is claimed is:

1. An implantable prosthesis having a lumen, said implantable prosthesis comprising:
   at least one radially-expandable tubular body having a first open end, a second open end, and a sidewall extending therebetween; and
   at least one skirt extending from, and at least partially overlapping, said tubular body, said skirt terminating in a peripheral edge that is spaced from a juncture between said skirt and said tubular body, at least portions of said peripheral edge being free and displaceable to a greater diameter than said tubular body, said skirt extending from said juncture towards said first end, wherein at least one hole is defined through said sidewall which is overlapped by said skirt, said at least one hole communicating with said lumen of said implantable prosthesis, said sidewall having an uninterrupted outer surface between said first end and said at least one hole so as to allow blood flow trapped by said skirt to be introduced into said lumen of said implantable prosthesis via said at least one hole.

2. A prosthesis as in claim 1, wherein said skirt is at least partially supported by a scaffold.

3. A prosthesis as in claim 2, wherein said scaffold is at least partially formed of self-expandable material.

4. A prosthesis as in claim 2, wherein said scaffold includes a plurality of circumferentially-spaced tines which generally extend from said tubular body.

5. A prosthesis as in claim 4, wherein said tines are arcuate.

6. A prosthesis as in claim 1, wherein said skirt includes a first portion that is extendable circumferentially outwardly from said tubular body.

7. A prosthesis as in claim 6, wherein said first portion is at least partially trough-shaped such that force applied to said first portion in a direction generally parallel to said tubular body is partially re-directed to define a radial force directed away from said tubular body.

8. A prosthesis as in claim 1, wherein at least first and second skirts extend from, and overlap, said tubular body, said first and second skirts being disposed in opposite directions.

9. A prosthesis as in claim 8, wherein said first skirt extends from a juncture with said tubular body at a location closer to a first end of said tubular body than a second end of said tubular body.

10. A prosthesis as in claim 9, wherein said second skirt is supported by a scaffold.

11. A prosthesis as in claim 1, wherein a plurality of skirts extend from, and overlap, said tubular body.

12. A prosthesis as in claim 1, wherein said prosthesis includes a plurality of radially-expandable tubular bodies.

13. A prosthesis is in claim 12, further comprising at least one radially expandable support member disposed concentrically relative to said tubular bodies.

14. A prosthesis as in claim 1, further comprising at least one radially expandable support member disposed concentrically relative to said tubular body.

15. A prosthesis as in claim 1, wherein said implantable prosthesis is for treating an abdominal aortic aneurysm.

16. A prosthesis as in claim 1, wherein said skirt is formed of a material selected from the group consisting of polymeric material, textile, natural tissue, and combinations thereof.

17. An implantable prosthesis comprising:

at least one radially-expandable tubular body; and at least one skirt extending from, and at least partially overlapping, said tubular body, said skirt terminating in a peripheral edge that is spaced from a juncture between said skirt and said tubular body, at least portions of said peripheral edge being free and displaceable to a greater diameter than said tubular body, wherein said skirt includes a first portion that is extendable circumferentially outwardly from said tubular body to have at least portions thereof spaced from said tubular body, and a second portion extendable from said first portion to be spaced from, and at least partially coextend with, said tubular body, said second portion being oriented in a different direction from said first portion when extended.

18. A prosthesis as in claim 17, wherein said second portion is extendable to taper outwardly away from said tubular body.

19. The prosthesis as in claim 17, wherein said second portion is extendable to be generally parallel to said tubular body.

* * * * *